United States Patent [19]

Kiffel et al.

[11] Patent Number: 4,837,012
[45] Date of Patent: Jun. 6, 1989

[54] HAIR REVIVER COMPOSITION CONTAINING FILM-FORMING AMINO ACIDS

[75] Inventors: William G. Kiffel, Kenosha; Therese M. Tyson, Racine, both of Wis.

[73] Assignee: S. C. Johnson & Son, Inc., Racine, Wis.

[21] Appl. No.: 63,952

[22] Filed: Jun. 19, 1987

[51] Int. Cl.[4] ............................................... A61K 7/06
[52] U.S. Cl. ........................................ 424/70; 424/71; 514/494; 514/724; 514/880
[58] Field of Search ............................ 424/43, 70, 71; 514/494, 724, 784, 880

[56] References Cited

U.S. PATENT DOCUMENTS

| | | |
|---|---|---|
| 3,235,457 | 2/1966 | Laden . |
| 3,303,213 | 2/1967 | Kalopissis et al. . |
| 3,331,781 | 7/1967 | Kalopissis et al. . |
| 3,534,032 | 10/1970 | Kalopissis et al. . |
| 3,862,151 | 1/1975 | Furia et al. ............................ 514/880 |
| 3,899,288 | 8/1975 | Galerre ................................. 424/70 |
| 3,958,581 | 5/1976 | Abegg et al. . |
| 3,961,054 | 6/1976 | Furia et al. .......................... 424/245 |
| 4,035,513 | 7/1977 | Kumano . |
| 4,073,898 | 2/1978 | Bouillon et al. . |
| 4,201,235 | 5/1980 | Ciavatta . |
| 4,283,386 | 8/1981 | Van Scott et al. . |
| 4,363,797 | 12/1982 | Jacquet et al. . |
| 4,369,037 | 1/1983 | Matjunasa et al. ................ 424/47 |
| 4,412,943 | 11/1983 | Hirota et al. . |
| 4,423,032 | 12/1983 | Abe et al. . |
| 4,459,284 | 7/1984 | Azuma et al. . |
| 4,465,664 | 8/1984 | Matsunaga et al. . |
| 4,530,829 | 7/1985 | Abe . |
| 4,536,390 | 8/1985 | Padden . |
| 4,592,907 | 6/1986 | Akimoto et al. ................... 424/70 |

FOREIGN PATENT DOCUMENTS 1063761  5/1958  Fed. Rep. of Germany ........ 424/70

Primary Examiner—Ellis P. Robinson
Assistant Examiner—P. J. Ryan

[57] ABSTRACT

A method of reviving unwashed, oily hair comprising applying to the hair a spray mist of a composition consisting essentially of at least one film-forming amino acid metal salt to give hair added body and a conditioning effect.

14 Claims, 3 Drawing Sheets

HAIR REVIVER COMPOSITION CONTAINING FILM-FORMING AMINO ACIDS

BACKGROUND OF THE INVENTION

This invention relates to a method of reviving unwashed, oily hair by applying to the hair a composition containing film-forming amino acid metal salts. More particularly, this invention relates to the use of film-forming amino acid metal salts in a cosmetically acceptable vehicle to give hair added body and a conditioning effect.

Hair revivers are products intended to improve the appearance of the hair, between shampoos. They are primarily used to cleanse or revive the hair at the end of the day and prior to a busy evening schedule. These products often contain a significant amount of talcum powder or rice starch to absorb oil. Such ingredients tend to flake away from the hair giving unsightly appearance to the clothes and tend to make dark hair take on a gray appearance.

Amino acids have previously been used in hair care products. For example, Abegg, U.S. Pat. No. 3,958,581 entitled "Cosmetic Composition Containing a Cationic Polymer and Divalent Metal Salt for Strengthening the Hair" discloses a hair strengthening composition containing a cationic polymer, a cationic polymer of selected divalent metal salts, and optionally amino acids. The Abegg composition is not, however, a reviver product, but instead, a product used to repair hair damaged from chemical treatment.

Azuma, U.S. Pat. No. 4,459,284 entitled "Permanent Composition Comprising Amino Acids" teaches a permanent waving composition of thioglycolic acid and an amino acid. The amino acid merely acts to increase the main effects of thioglycolic acid on keratin, decreases the need to use additional hair treatments and ameliorates the formation of worn out, discolored hair and skin damage, caused by the action of thioglycolic acid.

Accordingly, a need exists for an easy-to-apply, convenient-to-use hair reviver product that gives added body to hair.

It is an object of this invention to provide a hair reviver composition to improve the appearance of the hair which is easy to use, takes little time to apply and dry, provides easy combing or brushing, removes the stranding, greasy look of oily hair, and leaves the hair manageable, full and bouncy.

SUMMARY OF THE INVENTION

The attainment of one or more of the above objects is made possible by this invention which includes:

In a first embodiment, this invention relates to a method of reviving unwashed, oily hair to give it added body and a conditioned effect comprising applying to said hair, preferably via a spray mist, a composition consisting essentially of at least one film-forming amino acid metal salt in a cosmetically acceptable vehicle. In a second embodiment, this invention comprises applying to unwashed, oily hair a composition consisting essentially of at least one film-forming amino acid metal salt, a solvent carrier, and a conventional film-forming polymer. In still another embodiment, the above compositions further consist of precipitated amorphous hydrated silicon dioxide.

It has been unexpectedly found that the amino acid metal salts used in accordance with the teachings of this invention exhibit film-forming properties that translate into added body and fullness when applied to hair. The increase in fullness is especially noticeable when the method is used by persons having oily, fine-textured hair.

BRIEF DESCRIPTION OF THE DRWINGS

FIG. 1 is a schematic of a thermogram obtained for Sample 1 of Example 7.
FIG. 2 is a schematic of a thermogram obtained for Sample 2 of Example 7.
FIG. 3 is a schematic of a thermogram obtained for Sample 3 of Example 7.

DETAILED DESCRIPTION OF THE INVENTION

Figure 1:
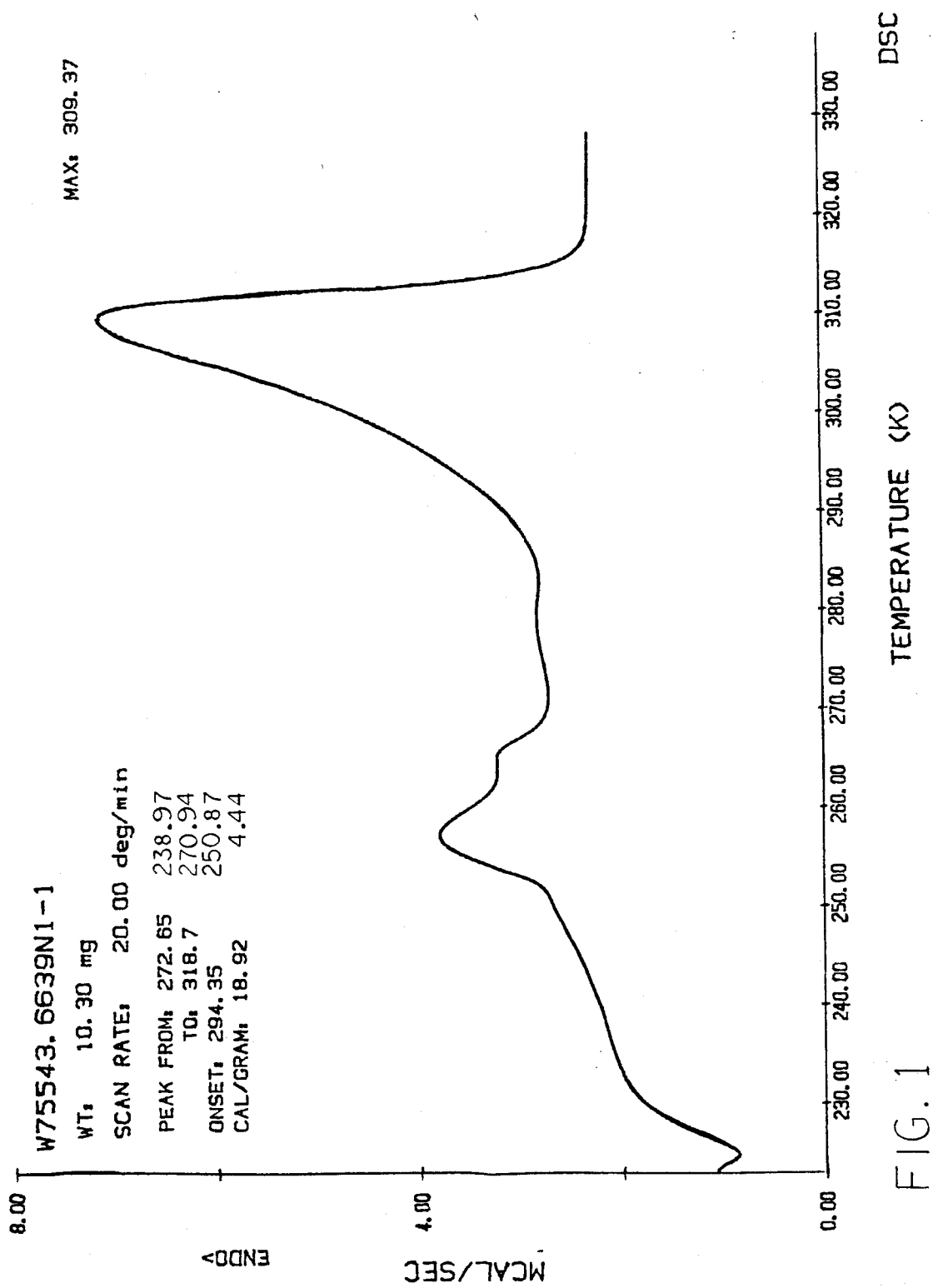

The method of reviving unwashed, oily hair comprises applying to the hair, preferably via a spray mist, a composition consisting essentially of at least one film-forming amino acid metal salt in a cosmetically acceptable vehicle. The concentration of amino acid metal salt utilized in accordance with the application method of this invention is not critical, and can vary from about 0.1 to 5% by weight, based on the total weight of the composition. The lower limit is defined by that amount required to give a film-forming effect and the upper limit, by economic considerations. Preferred amounts of film-forming amino acid metal salts are from about 1 to 2% by weight. Unless otherwise indicated, all percentages of ingredients are calculated as weight percentages based on the total weight of the hair reviver composition.

The metal salts of amino acids have been surprisingly found to display film-forming properties. These amino acids include Beta-alanine, L-alanine, L-proline, L-histidine, L-asparagine, L-threonine, L-serine, L-citrulline, L-carnosine, L-glutamic acid, L-aspartic acid, and mixtures thereof. The preferred metals of these amino acid metal salts are magnesium, calcium, potassium, sodium, zinc, barium, and mixtures thereof. The magnesium salts of L-aspartic acid and the calcium salts of L-glutamic acid are especially preferred. While the foregoing amino acids have been described in terms of the L("levo")-stereoisomer, D("dextro")-stereoisomers or mixtures of both stereoisomers of such amino acids can also be used. As is noted in Example 1 below, some of the amino acid metal salts formed hard films while other formed waxy films. Thus, the film properties can be modified by including mixtures of amino acid metal salts of each type.

The carrier material for the above-mentioned film-forming amino acid metal salts is present in an amount from about 80 to 99.99% by weight of the reviver composition. The carrier material can include water, or any cosmetically acceptable solvent material, such as the lower alkanols such as ethanol and isopropanol, and mixtures thereof. Preferred amounts of carrier material are given in the Examples below. A source of water is preferred for the practice of this invention so that films of the amino acid metal salts are formed on the hair. Moisture present in the hair can serve as a water source if none is included in the carrier material, Preferably, the hair is damp, such as after spraying a mist of water on the hair, prior to application if no water is present in the composition.

Other ingredients that may be added are conventional film-forming polymers, such as polyvinylpyrrolidone-quaternized amino acrylate or amino methacrylate copolymer, polyvinylpyrrolidone-vinyl acetate copolymer, linear polymers of 1-vinyl-2-pyrrolidone monomers, octylacrylamide/acrylates/ butylaminoethyl/ methacrylate copolymer, hydroxyethylcellulose and diallyldimethyl ammonium chloride copolymer and the like, and mixtures thereof. These hair-holding or film-forming polymers are well known in the art and are described in patents such as U.S. Pat. No. 4,536,390 (cols. 2-3), which is herein incorporated by reference. These film-forming polymers are used in amounts from about 0.01 to 3% by weight of the total composition, with preferred amounts ranging from about 0.1 to 1.5%. These polymers complement the film-forming properties of the amino acid metal salts by binding the amino acid metal salts to the hair and enhancing their hair holding properties.

Another ingredient that may be added to complement the film-forming amino acid metal salts is precipitated amorphous hydrated silicon dioxide. The concentration of this silicon dioxide ingredient can range from about 0.05 to 1% by weight, with more preferred amounts given in the Examples below. An especially preferred precipitated amorphous hydrated silicon dioxide is Zeothix 265 from J.M. Huber Corporation, Havre de Grace, Maryland. Zeothix 265 is characterized as follows: 1.5-2.0 micrometer average particle size, 200-300 $m^2/g$ surface area B.E.T., 2.0 g/ml density at 25° C., 1.45-1.46 refractive index, bulk density (packed) of 5-7 pounds per cubic foot, and an oil absorption capacity of 200-240 cc/100g. This ingredient helps prevent greasy hair by absorbing excess oil. Other conventional oil absorbing materials such as rice starch could also be used.

It was also found that the addition of certain plasticizers to the compositions of the present invention could modify the tactile feel of the hair treated with the compositions of the present invention and make the compositions useful for less oily hair. Thus, 0.05-1% by weight—based on the total weight of the composition -- of a plasticizer such as olive oil, squalene, coconut oil, glycerol, linoleic acid, oleic acid and mixtures thereof could be included for the above purpose.

It is important that the method of spray mist application of this invention does not excessively wet or dampen the hair. Excessive wetness may destroy the style or change the texture of the hair, thereby requiring a resetting or redrying of the hair, which would defeat the benefit of the present invention. Any of the conventional methods of application, a liquid or gel, mousse, non-aerosol pumps or aerosol spray containers, can be utilized in accordance with the teachings of this invention. Spray mist application is preferred.

The following Examples are provided to illustrate the present invention in accordance with the principles of this invention, but are not to be construed as limiting the invention.

EXAMPLE 1

Film-Forming Amino Acid Metal Salts

The film-forming properties of amino acids and amino acid metal salts were observed on black glass plates as follows. The 23 amino acids tested were L-alanine, Beta-alanine, L-aspartic acid, L-aparagine, L-carnosine, L-glutamic acid, L-proline, L-serine, L-threonine, L-citrulline, L-histidine HCl, L-arginine, L-cystine, glycine, L-isoleucine, L-leucine, L-lysine HCl, DL-methionine, L-methionie, L-phenylalanine, L-ornithine HCl, L-tyrosine and L-valine.

A solution containing 2% amino acid was prepared for each of the above amino acids by mixing 2 grams of the amino acid with 97.9 grams of water and 0.1 grams of formaldehyde. Approximately 1 gram of each solution was then applied to a clean black glass plate, allowed to air dry overnight at 75° F. and normal room humidity, and observed the next day at 75° F. and normal room humidity. All 23 of the 2% amino acid solutions prepared and tested as described formed white powdery or white crystalline residues on the black glass plates. None of the amino acids tested formed films.

0.5 grams of magnesium chloride was dissolved into the remaining portion of each amino acid solution to obtain magnesium salts of the amino acids. 1 gram of each resulting solution was applied to a black glass plate, allowed to air dry overnight at 75° F. and normal room humidity and observed the next day at 75° F. and normal room humidity. Films were formed by the magnesium salts of the following 9 of the 23 amino acids tested having the following character:

L-alanine - waxy film
Beta-alanine - cloudy, hard film
L-aspartic acid - hard, clear film
L-asparagine - waxy, cloudy film
L-carnosine - tacky, clear film
L-glutamic acid - hard, clear film
L-proline - thin, waxy film
L-serine - waxy film
L-threonine - waxy film The level of magnesium chloride in each of the solutions was increased to about 1% by again adding 0.5 grams of magnesium chloride to the remaining portion of each amino acid salt solution prepared above. The above black glass plate test was again repeated. Films were again formed by the above 9 amino acid salts and, in addition, the following formed films:

L-citrulline - thin, soft, wet film
L-histidine HCl - thin, soft film

It was observed that, at the higher (1%) level of magnesium chloride, the magnesium salts of L-threonine, L-alanine, L-histidine, and L-proline produced the least tacky films.

Additionally, waxy films were formed by the magnesium salts of the following amino acids: L-threonine, L-alanine, Beta-alanine, L-asparagine and L-serine. Film formation at 75° F. and normal room humidity is best demonstrated by magnesium salts of L-carnosine, L-aspartic acid, L-citrulline, and L-glutamic acid.

In another experiment, a solution of 2 grams of calcium di-L-glutamate, 0.1 grams of formaldehyde and 97.9 grams of water was prepared. Approximately 1 gram of that solution was applied to a clean black glass plate, allowed to air dry overnight at 75° F. and normal room humidity. The solution was found to have formed a clear, hard film when observed the next day at 75° F. and normal room humidity.

EXAMPLE 2

High Humidity Curl Relaxation Tests

High humidity curl relaxation tests were conducted comparing the application of film-forming amino acid metal salts of this invention, in particular the magnesium salts of L-aspartic acid, with several commercially available hair spray resins, i.e., Amphomer from National Starch and Chemical Corporation, PVP/VA E-535 and PVP/VA E-735 from GAF Corporation, and PVP-K60 also from GAF. PVP/VA E-535 and E-735 are well known copolymers of vinyl acetate and vinyl pyrrolidone from GAF. PVP/K-60 also from GAF is a linear polymer made from 1-vinyl-2-pyrrolidone. Amphomer from National Starch is an octylacrylamide/acrylates/ butylaminoethyl methacrylate copolymer formed from octylacrylamide, t-butylaminoethyl methacrylate and two or more monomers consisting of acrylic acid, methacrylic acid or any of their sample esters.

Each of the 5 formulations (magnesium aspartate, PVP/VA E-535, PVP/VA E-735, PVP-K60 and Amphomer) contained 1.5% of resin or amino acid metal salt in a carrier that consisted of a 1:1 mixture of deionized water and ethanol. The formulation containing Amphomer additionally contained 0.25% AMP-95. AMP-95, from International Minerals & Chemicals Corporation, is a substituted aliphatic alcohol (aminomethyl propanol) that conforms to the formula $(CH_3)_2NH_2CCH_2OH$.

The curl relaxation test was conducted in the following manner: Hair swatches 12 inches long and weighing approximately 2 grams were cut, curled using mandrels and placed in 100° F. oven to dry overnight. The wrapped mandrels were then allowed to cool at room temperature for 1 hour before the hair swatch was removed. Next, the swatch was attached to an agitator and rotated while being sprayed with approximately 2 grams of one of the formulations. After spraying, the swatch was left to dry without agitation for 3 minutes, placed on a tray, and left to dry for approximately 45 minutes before being placed in a humidity chamber. The swatches were hung in the chamber, one side of which contained a translucent piece of plastic marked in half centimeter squares. An initial curl reading (Lo) was taken, and additional readings of curl relaxation were taken at 5, 15, 30, 60 and 90 minutes (Lx). The swatch was then removed from the chamber and its total length measured (L). The curl relaxation was then determined by the following formula.

$$\frac{(Lx - Lo)}{(L - Lo)} \times 100$$

The curl relaxation properties of the 5 formulations were measured at a relative humidity of 96% at intervals of 5, 15, 30, 60 and 90 minutes. The results showed that at a relative humidity of 96% over a period of 90 minutes, a formulation applied by the method of this invention—the one containing 1.5% magnesium aspartate—gave a better curl hold at high humidity than the same method of application of those formulations containing PVP/VA E-735 and PVP/VA E-535 and gave substantially the same result as a formulation containing PVP-K60. The magnesium di-L-aspartate formulation did not, however, provide an equal or superior curl holding result compared to the formulation containing Amphomer, which is considered one of the most humidity resistant hair spray resins on today's market.

EXAMPLE 3

Other formulations within the scope of this invention are as follows:

|  | Concentrations | |
| Ingredients | Formula A | Formula B |
| --- | --- | --- |
| Deionized Water | 28.15 | 20.00 |
| Zeothix 265 | 0.25 | 0.50 |
| K/Mg L-Aspartate[1] | 1.00 | 3.00 |
| Gafquat 755N[2] | 0.50 | 0.50 |
| Ethanol | 70.00 | 75.90 |
| Fragrance | 0.10 | 0.10 |

[1]K/Mg L-Aspartate consisted of a 1:1 mole:mole mixture of potassium L-aspartate and magnesium di-L-aspartate.
[2]GAFQUAT 755N from GAF Corporation is an aqueous solution of a quaternary ammonium polymer formed by the reaction of dimethyl sulfate and a copolymer of vinyl pyrrolidone and dimethyl aminoethyl methacrylate, having a weight average molecular weight of greater than 1,000,000 and having a solids content of about 20%.

To prepare Formulas A and B, the Zeothix was first added to water, agitated and heated (about 110° F.) until dispersed. The aspartic acid salts and Gafquat 755N were then separately added with agitation until each dissolved. The ethanol and fragrance were premixed and added to the above mixture.

After applying these liquid formulas to dirty hair with a pump spray, the hair was then brushed and blow dried. The product gave body and fullness to the hair by lifting it away from the scalp, and the stranding or greasy look was eliminated. The product also seemed to smooth the frizzy ends of permed hair and gave a more conditioned look. The biggest improvements were noted with fine, oil hair.

EXAMPLE 4

Still other formulations of this invention are shown in Formulas C and D.

|  | Concentrations | |
| Ingredients | Formula C | Formula D |
| --- | --- | --- |
| Deionized Water | 28.40 | 28.05 |
| Ethanol | 70.00 | 70.00 |
| Zeothix 265[1] | 0.25 | 0.25 |
| Luvitol HP | 0.10 | 0.10 |
| Croquat M[2] | 0.25 | 0.50 |
| K/Mg L-aspartate[3] | 1.00 | 1.00 |
| Fragrance | — | 0.10 |

[1]Luvitol HP is a hydrogenated polyisobutene manufactured by BASF Wyandotte Corporation.
[2]Croquat M is cocodiammonium hydrolyzed animal protein (bovine collagen skin) of molecular weight 2,500 produced by Croda, Inc.
[3]The K/Mg L-Aspartate consisted of a 1:1 mole:mole mixture of potassium L-aspartate and magnesium di-L-aspartate.

These formulations were prepared by first adding the Zeothix 265 to water, agitating and heating the mixture (about 110° F.) until it dispersed. K/Mg L-aspartate and Croquat M were then separately added with agitation after each addition. The mixture was cooled to room temperature and a mixture of ethanol, Luvitol HP and fragrance was combined with it.

EXAMPLE 5

Formula E was prepared by heating the water to 110° F. and separately adding the magnesium di-L-glutamate and Croquat M with agitation after each addition. The mixture was then cooled to room temperature and ethanol, which was previously combined with the fragrance, was added to the above mixture.

| Ingredients | Concentrations Formula E |
| --- | --- |
| Deionized Water | 48.40 |

-continued

| Ingredients | Concentrations Formula E |
|---|---|
| Mg L-glutamate | 1.00 |
| Croquat M | 0.50 |
| Ethanol | 50.00 |
| Fragrance | 0.10 |

Use of the formula resulted in improved body and hair-holding properties.

All of the above formulas were prepared as non-aerosols, which is the preferred product dispensing form of this invention.

EXAMPLE 6

Formula F was prepared by heating the water to 100° F. and separately adding the Zeothix 265, Mg di-L-aspartate and Croquat M with agitation after each addition. The mixture was then cooled to room temperature and ethanol, which was previously combined with the Luvitol HP and the fragrance, was added to the above mixture.

| Ingredients | Concentrations Formula F |
|---|---|
| Deionized water | 28.05 |
| Zeothix 265 | 0.25 |
| Mg di-l-aspartate | 1.00 |
| Croquat M | 0.50 |
| Ethanol | 70.00 |
| Fragrance | 0.10 |
| Luvitol HP | 0.10 |

The above formula was evaluated by a user panel of 50 women who were asked to use the product at least twice during the one week test period. The results were that although less than a quarter of the evaluators reported that the hair felt "sticky", "not clean", and/or "felt dry/stiff", about the same number of the evaluators found that the formulation produced added body to the hair and improved style hold, and a little over one-third ranked convenience and ease of use as a benefit. These results were for a product which is intended to be used on oily hair which has not been washed and such hair is therefore somewhat harder to manage than newly shampooed hair.

EXAMPLE 7

In this example, the effect of magnesium di-L-aspartate on the melting point of Spangler's Sebum Mixture was evaluated. Spangler's Sebum Mixture is used in the cosmetics industry to simulate the natural sebum produced by humans and has the following composition in percent by weight of each component:

| Ingredient | Percent by Weight |
|---|---|
| Palmitic acid | 13.3% |
| Stearic acid | 1.7% |
| Coconut oil | 15.0% |
| Paraffin | 10.0% |
| Spermacetti wax | 15.0% |
| Olive oil | 20.0% |
| Squalene | 5.0% |
| Cholesterol | 5.0% |
| Oleic acid | 10.0% |
| Linoleic | 5.0% |
| | 100.0% |

To prepare a sample of Spangler's Sebum Mixture containing magnesium di-L-aspartate, a mixture of the following was prepared:

| Ingredient | Parts by Weight |
|---|---|
| Ethanol | 46.5 |
| Deionized water | 50.0 |
| Spangler's Sebum Mixture | 0.5 |
| Magnesium di-L-aspartate | 3.0 |

This mixture was heated to 57° C. with agitation and the ethanol and water were evaporated away to recover a solid residue ("Sebum/Magnesium di-L-aspartate") for use in a melting point study.

Figure 2:
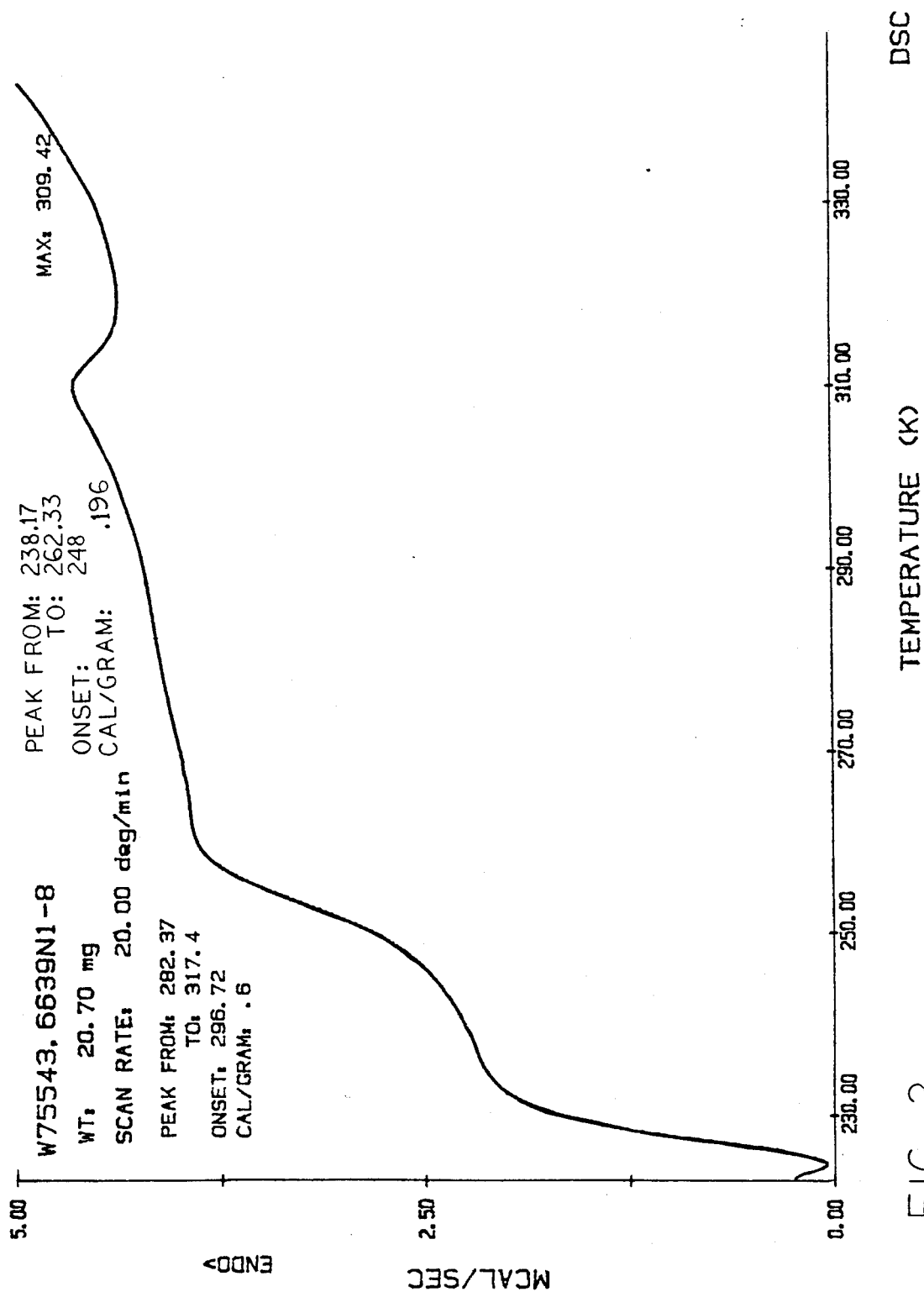
Figure 3:
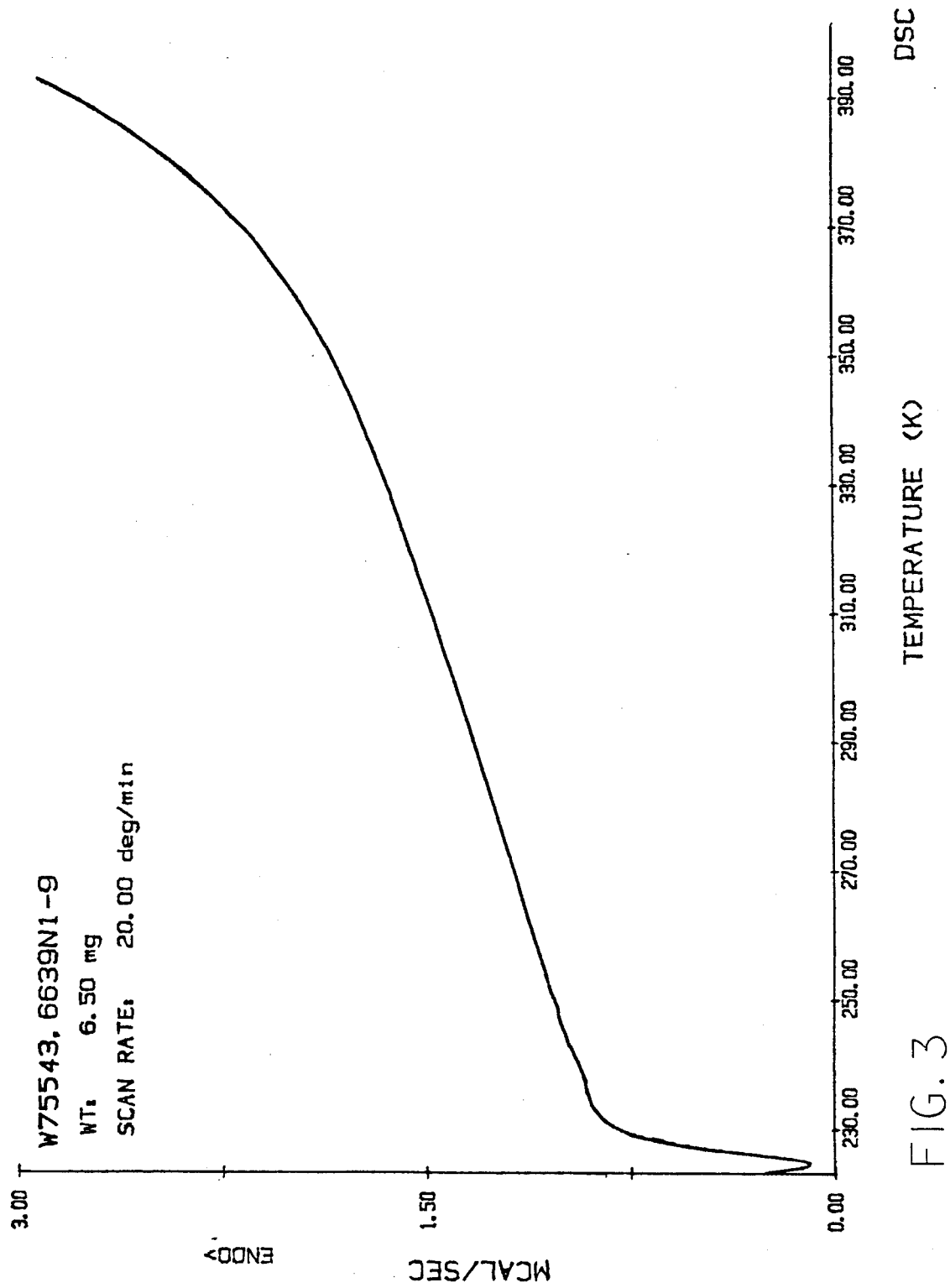

A Differential Scanning Calorimeter instrument, Model No. DSC-2C, made by Perkin-Elmer was used to determine the melting point range and the number of calories per gram required to melt three samples: the Spangler's sebum mixture described above (Sample 1), the Sebum/Magnesium di-L-aspartate sample (Sample 2), and the Magnesium di-L-aspartate itself (Sample 3). The instrument was set at a scan rate of 20.00 deg./min. over a range of 220.00 to 330.00° K. (−53.16° C. to 56.84° C.). FIG. 1 shows the thermogram obtained from Sample 1. FIG. 2 shows the thermogram from Sample 2 and FIG. 3 shows the thermogram from Sample 3. In summary, the results were as follows:

| Sample | Size* | Melt Onset °C. | Cal/Gram | Max. °C. |
|---|---|---|---|---|
| 1 | 10.3 | | −22 | 4.4 | −16 |
| 1 | 10.3 | | 21 | 18.9 | 36 |
| 2 | 20.7 | Tg at | −25 | 0.2 | — |
| 2 | 20.7 | | 24 | 0.6 | 36 |
| 3 | 6.5 | No thermal event obtained | | |

*sample size in milligrams

The results shown above and in FIGS. 1-3 indicate that a glass transition temperature—Tg—(first figure in the table for Sample 2) of the Spangler's Sebum Mixture (Sample 1–FIG. 1) is observed when magnesium di-L-aspartate, which itself has no melting point or glass transition temperature in the temperature range studied (Sample 3 FIG. 3), was added to the Spangler's Sebum Mixture (Sample 1) which itself exhibited no glass transition temperature in the temperature range studied. The presence of the magnesium di-L-aspartate did significantly reduce the number of calories per gram needed to melt the Spangler's Sebum Mixture. The significance of this observation is that the addition of the magnesium di-L-aspartate changes the character of the Spangler's Sebum Mixture.

EXAMPLE 8

In this example, swatches of DeMeo European Virgin Hair obtained from DeMeo Brothers, New York, NY were coated with Spangler's Sebum Mixture. The effect of compositions of the present invention containing magnesium di-L-aspartate on the hair volume versus control samples after air-drying and hot air blow drying was evaluated using a video imaging technique.

An aerosol dispenser container was filled with the following composition and pressurized ("Sebum Spray"):

| Ingredients | % by weight |
|---|---|
| Spangler's Sebum Mixture | 5.0 |

| Ingredients | % by weight |
|---|---|
| 1,1,1-trichloroethane | 65.0 |
| SD alcohol 40 (denatured ethanol) | 10.0 |
| Isobutane/propane mixture[1] | 20.0 |

[1]A-46 from Aeropres Corporation

Clean, dry swatches of DeMeo European Virgin Hair, five inches long, were weighed and evenly sprayed with Sebum Spray until 0.05 grams of the spray was deposited on each swatch. Each swatch was combed through using 20 downward strokes through the front of the swatch and 10 strokes at 90° relative to the front. To evenly distribute the deposited sebum mixture, each swatch was allowed to air dry 12 hours at room temperature while hanging from a holder. After air drying, a comb (teeth at 45% relative to the central long axis of the swatch) was then run down through the hair swatch using one stroke on each of the four sides (i.e., 90% apart). A videocamera image of each swatch was taken from the front and then at 90% from the front. The videocamera images were calibrated and interfaced with computer analysis equipment to allow the volume of the hair swatch to be calculated.

Each treated hair swatch, processed as above, was attached to the spindle of a rotating laboratory mixer. A blow dryer set at low speed was placed in front of the hair swatch to permit a stream of air at 105° F. (40° C.) to blow through the hair swatch while it was rotated at 40 r.p.m. Rotation was stopped after 1, 2, and 3 mintues and after each interval, the hair swatch was combed 10 strokes and the mixer motor was restarted. After the last interval, a comb (teeth at 45% relative to the central long axis of the swatch) was then run down through the hair swatch using one stroke on each of the four sides (i.e., 90% apart). Videocamera images of each hair swatch were again made as described above and the volume of each hair swatch was calculated.

The above samples were then treated with one of the following compositions:

| Ingredients | Concentration | |
|---|---|---|
| | Formula G | Formula H |
| Deionized water | 48.10 | 48.20 |
| Zeothix 265 | 0.10 | — |
| SD 40 Alcohol | 50.00 | 50.00 |
| Mg di-L-aspartate | 1.25 | 1.25 |
| Croquat M | 0.50 | 0.50 |
| Fragrance | 0.05 | 0.05 |

A pump sprayer was used to apply six pumps from a pump sprayer bottle (approximately 0.17 g per pump—0.9-1.1 g total) of Formulation G or H, respectively, to each of the blow dried hair swatches prepared as described above. Immediately after application, each hair swatch was combed using 10 strokes downward through the front of the swatch followed by 10 strokes downward through one side (90° to the front).

These swatches were then blow dried as described above. Videocamera images of each blow dried hair swatch were again made as described above and the volume of each hair swatch was again calculated by computer. The mean values for hair volume in area (two dimensional pictures were taken from two sides, 90° apart and calculated to give a measure of volume) was obtained for each swatch tested (in square centimeters) and are listed below:

| Swatch No. | Sebum Only A.D. | Sebum Only B.D. | Formula G B.D. | Formula H B.D. |
|---|---|---|---|---|
| 1 | 61.21 | 87.54 | — | 111.13 |
| 2 | 94.77 | 85.19 | — | 111.56 |
| 3 | 55.54 | 50.29 | — | 57.57 |
| 4 | 77.67 | 61.05 | 86.19 | — |
| 5 | 53.89 | 52.43 | 68.06 | — |
| 6 | 65.73 | 67.40 | 70.40 | — |
| 7 | 58.74 | 53.01 | 65.04 | — |

A.D. = Air Dried
B.D. = Blow-Dried

The results obtained indicate that blow drying the Sebum Only samples while they were spun generally reduced or had little effect on the hair volume except for Swatch No. 1. In all samples tested, the compositions of the present invention increase the hair volume. In most cases, the increase in hair volume was quite significant when compared with the blow dried Sebum Only swatches. Formula H, which was free of amorphous silicon dioxide, performed on a par with Formula G which contained amorphous silicon dioxide.

What is claimed is:

1. A method of reviving unwashed, oily hair to give it added body and a conditioned effect comprising applying to said hair a composition consisting essentially of about 0.01 to 5% by weight of at least one film-forming amino acid metal salt selected from the group consisting of metal salts of Beta-alanine, L-alanine, L-proline, L-histidine, L-asparagine, L-threonine, L-serine, L-citrulline, L-carnosine, L-glutamic acid, L-aspartic acid, a D-stereoisomer of any of the foregoing amino acid metal salts, and mixtures thereof, in a cosmetically acceptable vehicle wherein the metal of the film-forming amino acid metal salt is selected from the group consisting of magnesium, calcium, potassium, sodium, zinc, barium and mixtures thereof.

2. The method of claim 1 wherein the cosmetically acceptable vehicle consists of about 80 to 99.99% by weight of a carrier material selected from the group consisting of water, ethanol isopropanol, and mixtures thereof.

3. The method of claim 1 wherein the composition further consists of about 0.01 to 1% by weight of a precipitated amorphous hydrated silicon dioxide.

4. The method of claim 1 wherein the composition further consists of about 0.01 to 3% by weight of a film-forming polymer selected from the group consisting of polyvinylpyrrolidone-quaternized aminoacrylate copolymer, polyvinylpyrrolidone- quaternized aminomethacrylate copolymer, polyvinylpyrrolidone-vinyl acetate copolymer, linear polymers of 1-vinyl-2-pyrrolidone monomers, octylacrylamide/acrylates/butylaminoethyl/methacrylate copolymer, hydroxyethylcellulose and diallyldimethyl ammonium chloride copolymer, and mixtures thereof.

5. The method of claim 1 wherein the composition further consists of 0.25-0.5% by weight of cocodiammonium hydrolyzed animal protein.

6. The method of claim 1 wherein the composition is applied to the hair in the form of a spray mist.

7. The method of claim 1 wherein the composition further includes from 0.01 to 5% by weight of a plasticizer selected from the group consisting of olive oil, squalene, coconut oil, glycerol, linoleic acid, oleic acid, and mixtures thereof.

8. The method as claimed in claim 1 wherein the film-forming amino acid metal salt is selected from the group consisting of magnesium salts of L-aspartic acid, calcium salts of L-glutamic acid, and potassium salts of L-aspartic acid.

9. A method of reviving unwashed oily hair to give it added body and a conditioned effect comprising applying to said hair a spray mist of a composition consisting essentially of:
   (a) about 0.01 to 5% by weight of at least one film-forming amino acid metal salt selected from the group consisting of metal salts of Beta-alanine, L-alanine, L-proline, L-histidine, L-asparagine, L-threonine, L-serine, L-citrulline, L-carnosine, L-glutamic acid, L-aspartic acid, a D-stereoisomer of any of the foregoing amino acid metal salts, and mixtures thereof;
   (b) about 80 to 99.99% by weight of a carrier material selected from the group consisting of water, lower alkanols, and mixtures thereof; and
   (c) about 0.01 to 3% by weight of a film-forming polymer selected from the group consisting of polyvinylpyrrolidone-quaternized aminoacrylate copolymer, polyvinylpyrrolidone-quaternized aminomethacrylate copolymer, polyvinylpyrrolidone-vinylacetate copolymer, linear polymers of 1-vinyl-2-pyrrolidone monomers, octylacrylamide/acrylates/butylaminoethyl/methacrylate copolymer, hydroxyethylcellulose and diallyldimethyl ammonium chloride copolymer, and mixtures thereof,
wherein the metal of the film-forming amino acid metal salt is selected from the group consisting of magnesium, calcium, potassium, sodium, zinc, barium, and mixtures thereof.

10. The method of claim 9 wherein the composition further consists of 0.25–0.5% by weight of cocodiammonium hydrolyzed animal protein.

11. The method as claimed in claim 9 wherein the film-forming amino acid metal salt is selected from the group consisting of magnesium salts of L-aspartic acid, calcium salts of L-glutamic acid, and potassium salts of L-aspartic acid.

12. A method of reviving unwashed, oily hair to give it body and a conditioned effect comprising applying to said hair a spray mist of a composition consisting essentially of:
   (a) about 0.01 to 5% by weight of at least one film-forming amino acid metal salt selected group the group consisting of metal salts of Beta-alanine, L-alanine, L-proline, L-histidine, L-asparagine, L-threonine, L-serine, L-citrulline, L-carnosine, L-glutamic acid, L-aspartic acid, a d-stereoisomer of any of the foregoing amino acid metal salts, and mixtures thereof;
   (b) about 80 to 99.99% by weight of a carrier material selected from the group consisting of water, lower alkanols, and mixtures thereof;
   (c) about 0.01 to 1% by weight of a precipitated amorphous hydrated silicon dioxide; and
   (d) about 0.01 to 3% by weight of a film-forming polymer selected from the group consisting of polyvinylpyrrolidone-quaternized aminoacrylate copolymer, polyvinylpyrrolidone-quaternized aminomethacrylate copolymer, polyvinylpyrrolidone-vinylacetate copolymer, linear polymers of 1-vinyl-2-pyrrolidone monomers, octylacrylamide/acrylates/butylaminoethyl/methacrylate copolymer, hydroxyethylcellulose and diallyldimethyl ammonium chloride copolymer, and mixtures thereof,
wherein the metal of the film-forming amino acid metal salt is selected from the group consisting of magnesium, calcium, potassium, sodium, zinc, barium, and mixtures thereof.

13. The method of claim 12 wherein the composition further includes 0.01 to 5% by weight of a plasticizer selected from the group consisting of olive oil, squalene, coconut oil, glycerol, linoleic acid, oleic acid and mixtures thereof.

14. The method as claimed in claim 12 wherein the film-forming amino acid metal salt is selected from the group consisting of magnesium salts of L-aspartic acid, calcium salts of L-glutamic acid, and potassium salts of L-aspartic acid.

* * * * *